(12) United States Patent
Kawakami et al.

(10) Patent No.: US 11,077,069 B2
(45) Date of Patent: Aug. 3, 2021

(54) ADHESIVE POLYMER AND MEDICAL ADHESIVE PATCH

(71) Applicants: TEIKOKU SEIYAKU CO., LTD., Kagawa (JP); NIPPON SHOKUBAI CO., LTD., Osaka (JP)

(72) Inventors: Satoshi Kawakami, Sanuki (JP); Manabu Sogabe, Awa (JP); Taiki Shibata, Higashikagawa (JP); Yasushi Horikawa, Takamatsu (JP); Hiroaki Hasegawa, Ibaraki (JP)

(73) Assignees: TEIKOKU SEIYAKU CO., LTD, Kagawa (JP); NIPPON SHOKUBAI CO., LTD., Osaka (JP)

( * ) Notice: Subject to any disclaimer, the term of this patent is extended or adjusted under 35 U.S.C. 154(b) by 195 days.

(21) Appl. No.: 15/764,422

(22) PCT Filed: Sep. 30, 2016

(86) PCT No.: PCT/JP2016/079056
§ 371 (c)(1),
(2) Date: Mar. 29, 2018

(87) PCT Pub. No.: WO2017/057693
PCT Pub. Date: Apr. 6, 2017

(65) Prior Publication Data
US 2018/0280315 A1    Oct. 4, 2018

(30) Foreign Application Priority Data

Sep. 30, 2015 (JP) .............................. JP2015-193844

(51) Int. Cl.
| | | |
|---|---|---|
| *A61K 9/70* | (2006.01) | |
| *A61K 31/485* | (2006.01) | |
| *A61K 31/48* | (2006.01) | |
| *A61K 31/4468* | (2006.01) | |
| *A61K 31/4045* | (2006.01) | |
| *A61K 31/215* | (2006.01) | |
| *A61K 31/18* | (2006.01) | |
| *A61K 31/167* | (2006.01) | |
| *A61K 31/135* | (2006.01) | |
| *A61K 45/00* | (2006.01) | |
| *A61K 47/32* | (2006.01) | |
| *C08F 293/00* | (2006.01) | |
| *C09J 7/20* | (2018.01) | |
| *A61K 9/00* | (2006.01) | |

(52) U.S. Cl.
CPC .......... *A61K 9/7061* (2013.01); *A61K 9/0014* (2013.01); *A61K 9/7084* (2013.01); *A61K 31/135* (2013.01); *A61K 31/167* (2013.01); *A61K 31/18* (2013.01); *A61K 31/215* (2013.01); *A61K 31/4045* (2013.01); *A61K 31/4468* (2013.01); *A61K 31/48* (2013.01); *A61K 31/485* (2013.01); *A61K 45/00* (2013.01); *A61K 47/32* (2013.01); *C08F 293/00* (2013.01); *C09J 7/20* (2018.01)

(58) Field of Classification Search
CPC .. A61K 9/0014; A61K 9/7061; A61K 9/7084; A61K 31/135; A61K 31/215; A61K 31/4045; C08F 293/00; C09J 7/20; C07C 319/10; C07C 323/34
See application file for complete search history.

(56) References Cited

U.S. PATENT DOCUMENTS

| | | | |
|---|---|---|---|
| 4,954,343 A | 9/1990 | Hosaka et al. | |
| 5,679,762 A | 10/1997 | Yoshida et al. | |
| 5,869,598 A | 2/1999 | Yoshida et al. | |
| 6,669,953 B1 | 12/2003 | Kamiyama | |
| 2005/0214529 A1* | 9/2005 | Hasegawa ............. | C09J 153/00 428/343 |
| 2006/0052545 A1 | 3/2006 | Guerret et al. | |

(Continued)

FOREIGN PATENT DOCUMENTS

| | | |
|---|---|---|
| JP | 62-228008 | 10/1987 |
| JP | 6-199952 | 7/1994 |

(Continued)

OTHER PUBLICATIONS

Chinese Office Action in corresponding Chinese Patent Application No. 201680069496.5 dated Sep. 25, 2019, with English language translation.
"A Complete Collection on Organic Chemical Raw Materials (middle volume)", Wei Wende, Chemical Industry Press, p. 709, Jan. 31, 1999, cited in document CA (1999).
International Search Report dated Dec. 13, 2016 in International Application No. PCT/JP2016/079056.
International Preliminary Report on Patentability dated Apr. 12, 2018 in International Application No. PCT/JP2016/079056.
Extended European Search Report dated May 27, 2019 in European Patent Application No. 16851862.9.

(Continued)

*Primary Examiner* — Anna R Falkowitz
(74) *Attorney, Agent, or Firm* — Wenderoth, Lind & Ponack, L.L.P.

(57) ABSTRACT

The present invention provides a star-shaped acrylic block polymer having a star-shaped structure in which at least three chain polymer portions radiate from a mercapto group situated at the center, wherein (meth)acrylic acid alkyl ester structural units having 7-17 carbon atoms account for 30-99.9% by mass of whole structural units of the star-shaped acrylic block polymer, and at least one of the chain polymer portions has a copolymer structure of polymerizable monomers containing a (meth)acrylic acid alkyl ester having 7-17 carbon atoms and a weakly basic monomer; and a medical patch containing an adhesive composition containing a salt of a basic drug and the star-shaped acrylic block polymer as an adhesive that exhibits high drug efficacy, that does not cause a decrease in adhesive property of an adhesive base due to an additive, and that causes less skin irritation.

6 Claims, 1 Drawing Sheet

(56) References Cited

U.S. PATENT DOCUMENTS

| | | | |
|---|---|---|---|
| 2007/0026056 A1* | 2/2007 | Rolf | A61K 9/7061 |
| | | | 424/449 |
| 2008/0275375 A1 | 11/2008 | Guereet et al. | |
| 2011/0268785 A1 | 11/2011 | Wen et al. | |
| 2015/0182476 A1 | 7/2015 | Wen et al. | |

FOREIGN PATENT DOCUMENTS

| | | | |
|---|---|---|---|
| JP | 9-53059 | | 2/1997 |
| JP | 2842782 | | 1/1999 |
| JP | 2001-139646 | | 5/2001 |
| JP | 2001139646 | * | 5/2001 ............ C08F 293/00 |
| JP | 2001-512711 | | 8/2001 |
| JP | 3385177 | | 3/2003 |
| JP | 2006-500433 | | 1/2006 |
| JP | 4603398 | | 12/2010 |
| JP | 2011-51986 | | 3/2011 |
| JP | 4744481 | | 8/2011 |
| JP | 4916200 | | 4/2012 |
| JP | 49162200 | * | 4/2012 |
| JP | 2013-525432 | | 6/2013 |
| WO | 01/94490 | | 12/2001 |
| WO | 01/96411 | | 12/2001 |

OTHER PUBLICATIONS

Office Action dated Nov. 4, 2020 in corresponding Chinese Patent Application No. 201680069496.5, with English Translation.

Hou Xiuying et al., "A New Edition of Modern Practical Pharmacy", "Section 10 transdermal formulation", Xi'an Jiaotong University Press, 2015, pp. 196-204.

You Qidong et al., "Medicinal Chemistry", China Medical Science Press, 2011, pp. 570-571.

* cited by examiner

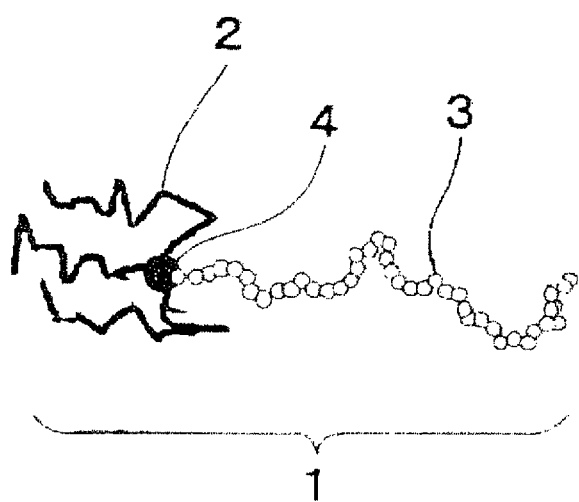

ADHESIVE POLYMER AND MEDICAL ADHESIVE PATCH

TECHNICAL FIELD

The present invention relates to a medical patch comprising a backing and an adhesive layer comprising an adhesive and a salt of a basic drug. More specifically, the present invention relates to a medical patch wherein the adhesive polymer as an adhesive is a star-shaped acrylic block polymer in which a weakly basic monomer is copolymerized.

BACKGROUND ART

A patch is a formulation for treating or preventing diseases by administering a drug in vivo, which can avoid the drug metabolism caused by a first-pass effect in tissues such as intestine and liver, which can decrease side effects, and which can continuously administer a drug over a long period of time. Especially, a transdermal formulation comprising a drug in an adhesive has been earnestly developed because it can be easily administered and strictly control the dose.

A medical patch consists of a backing, an adhesive layer (i.e., adhesive composition) comprising an adhesive base comprising an adhesive as the main ingredient and a drug, and a release liner. When a medical patch is used, a release liner is removed, and the patch is applied on an appropriate area. A medical patch must be adhered to a skin over a certain period of time in order to achieve sufficient transdermal permeation of a drug in the formulation, and thus is required to have sufficient adhesive force.

It is known that a drug contained in a medical patch can achieve higher transdermal absorbability when used in the form of free base as compared to being used in a salt form. However, many drugs are unstable in the form of free base, and the commercially available active pharmaceutical ingredients for medical use are often provided in a salt form.

It is reported that a drug in a salt form is converted into a free base in a patch by using a basic additive to increase the transdermal absorbability (Patent Document 1). However, addition of the additive may impair the properties of an adhesive base such as adhesive property and thermostability and decrease the adhesive force required for the adhesion to a skin. Further, when the basic additive is reacted with a salt of a basic drug, a basic salt is produced with a free base. However, some basic salts may crystallize in an intermediate product during the preparation process of the patch or in the patch, and may decrease the production efficiency and may impair the physical properties of the patch. Further, many basic salts by themselves cause skin irritation.

Meanwhile, Patent Document 2 discloses that an aminated methacrylic acid copolymer is contained in a patch to convert a salt of a basic drug into a free base in the patch. However, said method decreases the adhesive force of the patch.

Further, Patent Document 3 discloses a patch using an acrylic adhesive comprising (meth)acrylamide having an amino group as a copolymerizing component. However, the adhesive property of the patch is not good. Thus, it has been desired to provide a patch having an excellent drug-release property as well as excellent physical properties of the patch.

CITATION LIST

Patent Document
[Patent Document 1] JP 2011-051986 A
[Patent Document 2] JP 2013-525432 A
[Patent Document 3] JP S62-228008 A

SUMMARY OF INVENTION

Technical Problem

The present invention has been made to solve the above-mentioned conventional problems. An object of the present invention is to provide a patch exhibiting high drug efficacy, an unimpaired adhesive property, and decrease in skin irritation by using a weakly basic functional group in a star-shaped acrylic block polymer which enables the conversion of a salt of a basic drug into a free base without a basic additive in the patch.

Solution to Problem

The present inventors have earnestly studied to solve the above problems, and found that a medical patch comprising a salt of a basic drug having high drug efficacy, an unimpaired adhesive property of an adhesive base, and a decrease in skin irritation can be provided by using a star-shaped acrylic block polymer as an adhesive in which a weakly basic monomer is copolymerized in the medical patch. Especially, the present inventors have found for the first time that by using a star-shaped acrylic block polymer as an adhesive polymer having a copolymer structure comprising a weakly basic monomer as a polymerizable monomer in a patch comprising a drug, especially a basic drug, in contrast to the conventional star-shaped acrylic block polymers, the conventional problems of the physical properties of patch (for example, adhesive property and retention property) caused by the basic drug can be solved, and as a result, an excellent medical patch which can be applied to a skin over a long period of time, decreases skin irritation, and has a high drug-release property can be provided.

Namely, the aspects of the present invention are as follows.

Star-Shaped Acrylic Block Polymer and the Production Method Thereof

[1] A star-shaped acrylic block polymer having a star-shaped structure in which at least three chain polymer portions radiate from a sulfur residue of a mercapto group situated at the center, wherein (meth)acrylic acid alkyl ester structural units having 7-17 carbon atoms account for 30-99.9% by mass of whole structural units of said star-shaped acrylic block polymer, and at least one of said chain polymer portions has a structural unit having a copolymer structure of polymerizable monomers comprising a (meth)acrylic acid alkyl ester having 7-17 carbon atoms and a weakly basic monomer;

[1-1] The star-shaped acrylic block polymer according to the above [1], wherein the (meth)acrylic acid alkyl ester structural units having 7-17 carbon atoms account for 50-99.9% by mass of whole structural units of said star-shaped acrylic block polymer;

[1-a] A medical patch comprising an adhesive composition comprising a salt of a basic drug and an adhesive, characterized in that said adhesive is a star-shaped acrylic block polymer having a star-shaped structure in which at least three chain polymer portions radiate from a mercapto group situated at the center, and (meth)acrylic acid alkyl ester structural units having 7-17 carbon atoms account for 50-99.9% by mass of whole structural units of said polymer portions, and at least one of said chain polymer portions has a copolymer structure of polymerizable monomers comprising a (meth)acrylic acid alkyl ester having 7-17 carbon atoms and a weakly basic monomer;

[1-2] The star-shaped acrylic block polymer according to the above [1], wherein the polymerizable monomers may further comprise one or a combination of two or more selected from the group consisting of other polymerizable monomers and polyfunctional monomers;

[2] The star-shaped acrylic block polymer according to the above [1], wherein the content of the weakly basic monomer per whole structural units in said star-shaped acrylic block polymer is 0.1-39% by mass;

[3] The star-shaped acrylic block polymer according to the above [1] or [2], wherein the chain polymer portion comprises a polymeric structure of radical polymerizable monomers.

[4] The star-shaped acrylic block polymer according to any one of the above [1]-[3], wherein the (meth)acrylic acid alkyl ester having 7-17 carbon atoms is one or a combination of two or more selected from the group consisting of (meth)acrylic acid butyl ester, (meth)acrylic acid t-butyl ester, (meth)acrylic acid pentyl ester, (meth)acrylic acid hexyl ester, (meth)acrylic acid heptyl ester, (meth)acrylic acid octyl ester, (meth)acrylic acid isooctyl ester, (meth)acrylic acid nonyl ester, (meth)acrylic acid isononyl ester, (meth)acrylic acid decyl ester, (meth)acrylic acid undecyl ester, (meth)acrylic acid dodecyl ester, and (meth)acrylic acid 2-ethylhexyl ester;

[5] The star-shaped acrylic block polymer according to any one of the above [1]-[4], wherein the weakly basic monomer is one or a combination of two or more selected from the group consisting of (meth)acrylates having a tertiary amine as a side chain, and amides;

[6] The star-shaped acrylic block polymer according to any one of the above [1]-[5], wherein the weakly basic monomer is one or a combination of two or more selected from the group consisting of dimethylaminoethyl (meth)acrylate, diethylaminoethyl (meth)acrylate, dimethylaminoethyl (meth)acrylate quaternary ammonium salt, dimethylaminopropyl acrylamide, diethylaminopropyl acrylamide, (meth)acrylamide, N-methyl(meth)acrylamide, and N-propyl (meth)acrylamide;

[7] A method for producing a star-shaped acrylic block polymer characterized in that the star-shaped acrylic block polymer in which at least three chain polymer portions radiate from a sulfur residue of a mercapto group situated at the center according to any one of the above [1]-[6] is obtained by steps comprising:

the first polymerization step in which radical polymerization of polymerizable monomers is carried out in the presence of a polyvalent mercaptan; and the second polymerization step in which radical polymerization of an intermediate polymer obtained in said first polymerization step and polymerizable monomers is carried out, wherein in the second reaction stage of the first polymerization step and the second polymerization step, the polymer solution obtained in the first polymerization step and the polymerizable monomers used in the second polymerization step are preliminarily collectively mixed, and the polymerization of the second reaction stage is carried out using the resulting mixed solution.

Medical Patch

[8] A medical patch comprising an adhesive composition comprising a salt of a basic drug and an adhesive, characterized in that said adhesive is a star-shaped acrylic block polymer having a star-shaped structure in which at least three chain polymer portions radiate from a sulfur residue of a mercapto group situated at the center according to any one of the above [1]-[6], wherein (meth)acrylic acid alkyl ester structural units having 7-17 carbon atoms account for 30-99.9% by mass of whole structural units of said star-shaped acrylic block polymer, and at least one of said chain polymer portions has a structural unit having a copolymer structure of polymerizable monomers comprising a (meth)acrylic acid alkyl ester having 7-17 carbon atoms and a weakly basic monomer;

[9] The medical patch according to the above [8], wherein the content of the weakly basic monomer relative to non-volatile content in said adhesive is 0.1-39% by mass;

[10] The medical patch according to the above [8] or [9], wherein the content of the salt of the basic drug is 0.1-50% by mass, and the content of the adhesive is 50-99.9% by mass in the adhesive composition;

[11] The medical patch according to any one of the above [8]-[10], wherein the (meth)acrylic acid alkyl ester having 7-17 carbon atoms is one or a combination of two or more selected from the group consisting of (meth)acrylic acid butyl ester, (meth)acrylic acid t-butyl ester, (meth)acrylic acid pentyl ester, (meth)acrylic acid hexyl ester, (meth)acrylic acid heptyl ester, (meth)acrylic acid octyl ester, (meth)acrylic acid isooctyl ester, (meth)acrylic acid nonyl ester, (meth)acrylic acid isononyl ester, (meth)acrylic acid decyl ester, (meth)acrylic acid undecyl ester, (meth)acrylic acid dodecyl ester, and (meth)acrylic acid 2-ethylhexyl ester;

[12] The medical patch according to any one of the above [8]-[11], wherein the weakly basic monomer is one or a combination of two or more selected from the group consisting of dimethylaminoethyl (meth)acrylate, diethylaminoethyl (meth)acrylate, dimethylaminoethyl (meth)acrylate quaternary ammonium salt, dimethylaminopropyl acrylamide, diethylaminopropyl acrylamide, (meth)acrylamide, N-methyl(meth)acrylamide, and N-propyl(meth)acrylamide;

[13] The medical patch according to any one of the above [8]-[12], wherein the salt of the basic drug is one or a combination of two or more selected from the group consisting of fentanyl citrate, morphine sulfate, oxycodone hydrochloride, buprenorphine hydrochloride, oxybutynin hydrochloride, tamsulosin hydrochloride, tolterodine tartrate, rasagiline mesylate, pergolide mesylate, amantadine hydrochloride, trihexyphenidyl hydrochloride, ropinirole hydrochloride, lidocaine hydrochloride, procaine hydrochloride, donepezil hydrochloride, memantine hydrochloride, tandospirone citrate, methylphenidate hydrochloride, lurasidone hydrochloride, chlorpromazine hydrochloride, imipramine hydrochloride, asenapine maleate, salbutamol sulfate, clenbuterol hydrochloride, tulobuterol hydrochloride, procaterol hydrochloride, butorphanol tartrate, perisoxal citrate, enalapril maleate, propranolol hydrochloride, bisoprolol hydrochloride, clonidine hydrochloride, diltiazem hydrochloride, verapamil hydrochloride, isosorbide dinitrate, ketotifen fumarate, chlorpheniramine maleate, azelastine hydrochloride, diphenhydramine hydrochloride, granisetron hydrochloride, ramosetron hydrochloride, palonosetron hydrochloride, and ondansetron hydrochloride.

Other aspects of the present invention are as follows.

[14] The medical patch according to any one of the above [8]-[13], wherein the (meth)acrylic acid alkyl ester having 7-17 carbon atoms is one or a combination of two selected from the group consisting of acrylic acid butyl ester and acrylic acid 2-ethylhexyl ester;

[15] The medical patch according to any one of the above [8]-[14], wherein the weakly basic monomer is dimethylaminoethyl methacrylate or dimethylaminopropyl acrylamide; and

[16] The medical patch according to any one of the above [8]-[15], wherein the salt of the basic drug is rasagiline mesylate.

The still other aspects of the present invention are as follows.

[17] The medical patch according to any one of the above [8]-[16] which does not comprise a basic additive;

[18] A medical patch comprising an adhesive composition comprising a salt of a basic drug and an adhesive, characterized in that said adhesive is a star-shaped acrylic block polymer having a star-shaped structure in which at least three chain polymer portions radiate from a sulfur residue of a mercapto group situated at the center according to any one of the above [1]-[6], wherein (meth)acrylic acid alkyl ester structural units having 7-17 carbon atoms account for 30-99.9% by mass of whole structural units of said star-shaped acrylic block polymer, and at least one of said chain polymer portions has a structural unit having a copolymer structure of polymerizable monomers comprising a (meth) acrylic acid alkyl ester having 7-17 carbon atoms and a weakly basic monomer;

[19] The medical patch according to any one of the above [7]-[17], characterized in that the star-shaped acrylic block polymer in which at least three chain polymer portions radiate from a sulfur residue of a mercapto group situated at the center is obtained by steps comprising:

the first polymerization step in which radical polymerization of polymerizable monomers is carried out in the presence of a polyvalent mercaptan; and the second polymerization step in which radical polymerization of an intermediate polymer obtained in said first polymerization step and polymerizable monomers is carried out, wherein in the second reaction stage of the first polymerization step and the second polymerization step, the polymer solution obtained in the first polymerization step and the polymerizable monomers used in the second polymerization step are preliminarily collectively mixed, and the polymerization of the second reaction stage is carried out using the resulting mixed solution; and

[19] The method for producing the medical patch according to any one of the above [7]-[18], characterized in that the method comprises the steps:

(a) producing a star-shaped acrylic block polymer by two steps of radical polymerization consisting of the first polymerization step and the second polymerization step using the same or different kind of polymerizable monomer in each elementary step of the radical polymerization steps in the presence of a polyvalent mercaptan, wherein a weakly basic monomer is used in at least one elementary step of said two steps, and in the second step of said two steps, a part of a polymer solution obtained in the first step and polymerizable monomers used in the second step are polymerized, and then a monomer mixture comprising the remainder of the polymer solution obtained in the first step and the polymerizable monomers used in the second step is gradually added therein and mixed to be subjected to polymerization; and (b) mixing the star-shaped acrylic block polymer obtained in said (a) and a salt of a basic drug.

Effect of Invention

According to the present invention, a medical patch comprising a drug, especially a basic drug which can convert a salt of the basic drug into a free base in the formulation in high efficiency, exhibits a high drug-release property, does not decrease the adhesive property or retention property of an adhesive base, and has lowered skin irritation, can be provided without adding a basic additive (for example, amines such as diethanolamine; a basic salt such as sodium acetate; and a basic polymer such as aminoalkyl methacrylate polymer (for example, EUDRAGIT E-100)) by using a star-shaped acrylic block polymer as an adhesive in which a weakly basic monomer is copolymerized.

Namely, according to the medical patch provided by the present invention, a drug can be absorbed into circulating blood via a skin in high efficiency, and side effects in gastrointestinal system due to oral administration and side effects which may be caused by the rapid increase in blood concentration can be avoided.

BRIEF DESCRIPTION OF DRAWINGS

FIG. 1 shows an example of schematic diagram of a star-shaped acrylic block polymer of the present invention. The symbols in the FIGURE means 1: star-shaped structure, 2: chain polymer portions formed in the first polymerization step, 3: a chain polymer portion formed in the second polymerization step, and 4: a mercapto group.

DESCRIPTION OF EMBODIMENTS

The medical patch of the present invention can be prepared by using a star-shaped acrylic block polymer in which a weakly basic monomer is copolymerized acting as an adhesive polymer as an adhesive, and adding a salt of a basic drug as an active ingredient therein to obtain an adhesive layer as a composition (i.e., adhesive composition), and laminating the adhesive layer on a backing.

The above star-shaped acrylic block polymer (also referred to as star-shaped acrylic block copolymer) has a star-shaped structure in which at least three chain polymer portions radiate from a sulfur residue of a mercapto group situated at the center. Such star-shaped structure is also disclosed in documents (for example, JP 2842782 B2, JP 3385177 B2, JP 4603398 B2, JP 4744481 B2, and JP 4916200 B2). An example of schematic diagram of the star-shaped acrylic block polymer structure of the present invention is shown in FIG. 1. Also, (meth)acrylic acid alkyl ester structural units having 7-17 carbon atoms account for 30-99.9% by mass of whole structural units in said star-shaped acrylic block polymer. The content of the (meth) acrylic acid alkyl ester structural units having 7-17 carbon atoms in whole structural units of said star-shaped acrylic block polymer is preferably 60-99.9% by mass, 35-97% by mass, more preferably 70-99.9% by mass, 40-95% by mass, still more preferably 50-85% by mass. When the content of the (meth)acrylic acid alkyl ester structural units having 7-17 carbon atoms in whole structural units of said star-shaped acrylic block polymer is less than 50% by mass, the polymer does not have a sufficient adhesive force. In the present description, "(meth)acrylic acid" means acrylic acid or methacrylic acid, and "structural unit(s)" in a polymer portion means unit(s) consisting of a structure derived from polymerizable monomers constituting the polymer. The sulfur residue of said mercapto group situated at the center means the backbone per se derived from a polyvalent mercaptan having said sulfur residue.

In the present description, for example, "X-Y % by mass" in a numerical range means "X % by mass or more to Y % by mass or less" unless otherwise specified.

Examples of the polymerizable monomer corresponding to (meth)acrylic acid alkyl ester structural units having 7-17 carbon atoms (hereinafter also referred to as "(meth)acrylic acid alkyl ester monomer having 7-17 carbon atoms"), namely, (meth)acrylic acid alkyl ester having 7-17 carbon atoms include one or a combination of two or more selected from the group consisting of (meth)acrylic acid butyl ester, (meth)acrylic acid t-butyl ester, (meth)acrylic acid pentyl ester, (meth)acrylic acid hexyl ester, (meth)acrylic acid heptyl ester, (meth)acrylic acid octyl ester, (meth)acrylic acid isooctyl ester, (meth)acrylic acid nonyl ester, (meth)acrylic acid isononyl ester, (meth)acrylic acid decyl ester, (meth)acrylic acid undecyl ester, (meth)acrylic acid dodecyl ester, (meth)acrylic acid 2-ethylhexyl ester; and the like. Preferable examples of (meth)acrylic acid alkyl ester monomer having 7-17 carbon atoms include (meth)acrylic acid butyl ester, (meth)acrylic acid t-butyl ester, (meth)acrylic acid 2-ethylhexyl ester, (meth)acrylic acid octyl ester, (meth)acrylic acid isooctyl ester, (meth)acrylic acid nonyl ester, and (meth)acrylic acid isononyl ester, more preferable examples include a combination of (meth)acrylic acid butyl ester and (meth)acrylic acid 2-ethylhexyl ester, and still more preferable examples include a combination of acrylic acid butyl ester and acrylic acid 2-ethylhexyl ester. When the (meth)acrylic acid alkyl ester monomer having 7-17 carbon atoms is used as a first polymerizable monomer and a second polymerizable monomer, they may be the same or different from each other.

The weakly basic monomer means, for example, one or a combination of two or more selected from the group consisting of (meth)acrylates having a tertiary amine as a side chain, and amides. Examples of the weakly basic monomer include one or a combination of two or more selected from the group consisting of dialkylaminoalkyl (meth)acrylates such as dimethylaminoethyl (meth)acrylate and diethylaminoethyl (meth)acrylate; dialkylaminoalkyl (meth)acrylate quaternary ammonium salts such as dimethylaminoethyl (meth)acrylate quaternary ammonium salt: (meth)acrylamides such as dimethylaminopropyl acrylamide, diethylaminopropyl acrylamide, (meth)acrylamide, N-methyl (meth)acrylamide, and N-propyl (meth)acrylamide; and the like. Preferable examples of the weakly basic monomer include dialkylaminoalkyl (meth)acrylates, (meth)aminoalkylacrylamides, and (meth)acrylamides, more preferable examples include dimethylaminoethyl (meth)acrylate, diethylaminoethyl (meth)acrylate, dimethylaminopropyl acrylamide, diethylaminopropyl acrylamide, (meth)acrylamide, N-methyl (meth)acrylamide, and N-propyl (meth)acrylamide, and still more preferable examples include dimethylaminoethyl methacrylate and dimethylaminopropyl acrylamide. When the weakly basic monomer is used as a first polymerizable monomer and a second polymerizable monomer, they may be the same or different from each other.

Any one of the above weakly basic monomers may be used alone, or in combination of two or more of them. The total content of the weakly basic monomer in whole structural units of the above star-shaped acrylic block polymer is 0.1-39% by mass, preferably 1-39% by mass, more preferably 1.5-39% by mass. Alternatively, the total content of the weakly basic monomer in whole structural units of a star-shaped acrylic block polymer is 0.1-39% by mass, preferably 1-39% by mass, more preferably 1.5-39% by mass. When the total content of the weakly basic monomer is less than 0.1% by mass, a salt of a basic drug is not converted into a free base. Meanwhile, when the total content of the weakly basic monomer is more than 39% by mass, the physical property balance as adhesive polymer is impaired.

The chain polymer portion comprises a polymeric structure of radical polymerizable monomers, wherein the radical polymerizable monomers are, for example, (meth)acrylic acid alkyl ester monomers having 7-17 carbon atoms, weakly basic monomers, and other polymerizable monomers.

The chain polymer portion of the star-shaped acrylic block polymer may comprise structural units derived from a polymerizable monomer other than the (meth)acrylic acid alkyl ester having 7-17 carbon atoms and the weakly basic monomer (hereinafter referred to as "another polymerizable monomer (or other polymerizable monomers)") and/or the following polyfunctional monomers in the content of less than 70% by mass, preferably less than 50% by mass in whole structural units, in addition to the weakly basic monomer.

Examples of other polymerizable monomers include polymerizable monomers which are homopolymerizable or copolymerizable by radical polymerization, and include one or a combination of two or more selected from the group consisting of (meth)acrylic acid alkyl esters having 6 or less carbon atoms such as methyl (meth)acrylate and ethyl (meth)acrylate; styrene monomers such as α-methylstyrene, vinyl toluene, and styrene; maleimide monomers such as phenylmaleimide and cyclohexylmaleimide; vinyl ether monomers such as methyl vinyl ether, ethyl vinyl ether, and isobutyl vinyl ether; fumaric acid monoalkyl esters and fumaric acid dialkyl esters; maleic acid monoalkyl esters and maleic acid dialkyl esters; itaconic acid monoalkyl esters and itaconic acid dialkyl esters; vinylpyrrolidones such as N-vinyl-2-pyrrolidone; (meth)acrylic acid alkoxy polyalkylene glycol esters such as methoxy triethylene glycol acrylate, methoxy polyethylene glycol methacrylate, ethoxy diethylene glycol acrylate, and methoxy polyethylene glycol acrylate; other vinyl compounds such as (meth)acrylonitrile, butadiene, isoprene, vinyl chloride, vinylidene chloride, vinyl acetate, vinyl ketone, vinyl pyridine, and vinyl carbazole; carboxyl group-containing monomers such as (meth)acrylic acid, fumaric acid, maleic acid, and itaconic acid; and the like. Preferable examples of the other polymerizable monomers include (meth)acrylic acid alkyl esters having 6 or less carbon atoms and vinyl compounds, and more preferable examples include methyl (meth)acrylate, ethyl (meth)acrylate, (meth)acrylonitrile, butadiene, isoprene, vinyl chloride, vinylidene chloride, vinyl acetate, vinyl ketone, vinyl pyridine, and vinyl carbazole, and still more preferable examples include methyl methacrylate and vinyl acetate. When the other polymerizable monomers are used as a first polymerizable monomer and a second polymerizable monomer, they may be the same or different from each other.

A polyfunctional monomer may be comprised in combination with the above "another polymerizable monomer (or other polymerizable monomers)", and examples of said polyfunctional monomer include one or a combination of two or more selected from the group consisting of diester compounds of diols and (meth)acrylic acids such as alkylene glycol di(meth)acrylate, ethylene glycol di(meth)acrylate, tetraethylene glycol di(meth)acrylate, polyethylene glycol di(meth)acrylate, propylene glycol di(meth)acrylate, polypropylene glycol (meth)acrylate, 1,3-butylene glycol di(meth)acrylate, 1,6-hexanediol di(meth)acrylate, neopentyl glycol di(meth)acrylate, 2-hydroxy-1,3-di(meth)acryloxypropane, 2,2-bis[4-(acryloxyethoxy)phenyl]propane, 2,2-bis[4-(methacryloxyethoxy)phenyl]propane, 2,2-bis[4-(acryloxy•polyethoxy)phenyl]propane, 2,2-bis[4-(methacryloxy•polyethoxy)phenyl]propane, and 2-hydroxy- 1-acryloxy-3-methacryloxypropane; polyester compounds of compounds having 3 or more hydroxy groups per one molecule and (meth)acrylic acids such as trimethylolpropane tri(meth)acrylate, tetramethylolmethane tri(meth)acrylate, tetramethylolmethane tetra(meth)acrylate, pentaerythritol tetrakis(meth)acrylate, and dipentaerythritol hexakis(meth)acrylate; allyl (meth)acrylate and divinylbenzene; and the like. Preferable examples of the polyfunctional monomer include tetraethylene glycol di(meth)acrylate, and more preferable examples include tetraethylene glycol di(meth)acrylate and ethylene glycol di(meth)acrylate. Each one of the above other polymerizable monomers and polyfunctional monomers may be used alone, or in combination of two or more of them.

In one typical embodiment of the star-shaped acrylic block polymer of the present invention, the (meth)acrylic acid alkyl ester having 7-17 carbon atoms is one or a combination of two or more selected from the group consisting of (meth)acrylic acid butyl ester and (meth)acrylic acid 2-ethylhexyl ester, and the weakly basic monomer is one or a combination of two or more selected from the group consisting of dialkylaminoalkyl (meth)acrylates and (meth)acrylamides.

In the embodiment, the radical polymerizable monomer constituting a certain polymer portion in at least three or more chain polymer portions is one or a combination of two or more selected from the group consisting of (meth)acrylic acid alkyl esters having 6 or less carbon atoms, and vinyl compounds.

In one typical embodiment of the star-shaped acrylic block polymer of the present invention, the (meth)acrylic acid alkyl ester having 7-17 carbon atoms is a combination of acrylic acid butyl ester and acrylic acid 2-ethylhexyl ester, and the weakly basic monomer is one or a combination of two or more selected from the group consisting of dimethylaminoethyl methacrylate and dimethylaminopropyl acrylamide.

In the embodiment, the radical polymerizable monomer constituting a certain polymer portion in at least three or more chain polymer portions is one or a combination of two or more selected from the group consisting of methyl methacrylate and vinyl acetate.

Due to the characteristic star-shaped acrylic block polymer structure, the star-shaped acrylic block polymer can achieve physical cross-linking caused by the microphase-separated structure, and achieve balanced adhesive force and cohesive force without using a cross-linking agent.

Hereinafter, an especially appropriate method for producing the star-shaped acrylic block polymer is described.

An especially appropriate method for producing the star-shaped acrylic block polymer includes a multistep radical polymerization method using a polyvalent mercaptan, wherein after the provision of all polymerizable monomers to a reaction system is completed, a polymerization initiator is subsequently added thereto. Such polymerization initiator subsequently added is referred to as "booster" in the present invention.

When the radical polymerization of the first polymerizable monomers (for example, any one of the (meth)acrylic acid alkyl ester monomers having 7-17 carbon atoms, the weakly basic monomers, or the other polymerizable monomers, or a mixture thereof, preferably the other polymerizable monomers alone) is carried out in the presence of a polyvalent mercaptan, the first polymerizable monomers are radically polymerized from a sulfur residue of a mercapto group of a polyvalent mercaptan as an origin, and chain polymer portions radiate from the sulfur residue of the mercapto group (in other words, a polyvalent mercaptan having said sulfur residue) situated at the center to form a first star-shaped structure. In such case, a part of valence of the sulfur residue of the mercapto group of the polyvalent mercaptan is not used as an origin of the radical polymerization and remains unreacted. Subsequently, when the second polymerizable monomers (for example, any one of the (meth)acrylic acid alkyl ester monomers having 7-17 carbon atoms, the weakly basic monomers, or the other polymerizable monomers, or the polyfunctional monomers, or a mixture thereof, preferably a mixture of the (meth)acrylic acid alkyl ester monomers having 7-17 carbon atoms, the weakly basic monomers, the other polymerizable monomers, and polyfunctional monomers) are added thereto to carry out the radical polymerization, the second polymerizable monomers are radically polymerized from the remaining sulfur residue of the mercapto group of the polyvalent mercaptan as an origin to form the second star-shaped structure different from the first star-shaped structure. As a result, the star-shaped acrylic block polymer of the present invention comprises at least three chain polymer portions.

In one typical embodiment of the method for producing the star-shaped acrylic block polymer of the present invention, in the first polymerization step, the polyvalent mercaptan is one or a combination of two or more selected from the group consisting of dipentaerythritol hexakisthioglycolate and dipentaerythritol hexakisthiopropionate (alias: dipentaerythritol-β-mercaptopropionate) (hereinafter abbreviate as DPMP), and the radical polymerizable monomer is another polymerizable monomer which is one or a combination of two or more selected from the group consisting of (meth)acrylic acid alkyl esters having 6 or less carbon atoms and vinyl compounds, and in the second polymerization step, the polymerizable monomer is a mixture of a (meth)acrylic acid alkyl ester having 7-17 carbon atoms which is one or a combination of two or more selected from the group consisting of (meth)acrylic acid butyl ester, (meth)acrylic acid t-butyl ester, and (meth)acrylic acid 2-ethylhexyl ester; a weakly basic monomer which is one or a combination of two or more selected from the group consisting of dialkylaminoalkyl (meth)acrylates and (meth)acrylamides; another polymerizable monomer which is one or a combination of two or more selected from the group consisting of (meth)acrylic acid alkyl esters having 6 or less carbon atoms and vinyl compounds; and a polyfunctional monomer selected from tetraethylene glycol di(meth)acrylate.

In one typical embodiment of the method for producing the star-shaped acrylic block polymer of the present invention, in the first polymerization step, the polyvalent mercaptan is dipentaerythritol hexakisthiopropionate, and the radical polymerizable monomer is another polymerizable monomer which is one or a combination of two or more selected from the group consisting of methyl methacrylate and vinyl acetate, in the second polymerization step, the polymerizable monomer is a mixture of (meth)acrylic acid alkyl ester having 7-17 carbon atoms which is one or a combination of two or more selected from the group consisting of acrylic acid butyl ester and acrylic acid 2-ethylhexyl ester; a weakly basic monomer which is one or a combination of two or more selected from the group consisting of dimethylaminoethyl methacrylate and dimethylaminopropyl acrylamide; another polymerizable monomer which is one or a combination of two or more selected from the group consisting of methyl methacrylate and vinyl acetate; and a polyfunctional monomer selected from tetraethylene glycol di(meth)acrylate.

In order to obtain the star-shaped acrylic block polymer, said multistep radical polymerization method especially preferably consists of two steps. Namely, said production method especially preferably comprises the first polymerization step in which radical polymerization of polymerizable monomers is carried out in the presence of a polyvalent mercaptan and the second polymerization step in which radical polymerization of an intermediate polymer obtained in said first polymerization step and polymerizable monomers is carried out, wherein (meth)acrylic acid alkyl ester having 7 or more carbon atoms accounts for 30-99.9% by mass of the total amount of all polymerizable monomers to be used, and a booster is added after the provision of all polymerizable monomers to a reaction system is completed.

In the second polymerization step, a polymer solution obtained in the first polymerization step is mixed with the polymerizable monomers used in the second polymerization step, and then polymerization is carried out.

In the second polymerization step, a polymer solution obtained in the first polymerization step and the polymerizable monomers used in the second polymerization step may be mixed at one time to be subjected to polymerization, or the polymerizable monomers used in the second polymerization step may be gradually added to and mixed with a polymer solution obtained in the first polymerization step.

In an especially preferable embodiment of the second polymerization step, to an initial preparation mixture (1) essentially comprising a part of (1a) a polymer solution obtained in the first polymerization step and (1b) the polymerizable monomers used in the second polymerization step is added a polymerization initiator to initiate the polymerization, and then a monomer mixture (2) essentially comprising the remainder of (2a) the polymer solution obtained in the first polymerization step and (2b) the polymerizable monomers used in the second polymerization step and a polymerization initiator are gradually added and mixed (preferably added dropwise and mixed) thereto, and after the addition and mixing are completed (namely, after the provision of all polymerizable monomers to the reaction system is completed), a booster is subsequently added thereto. Said method can sufficiently homogeneously mix the polymer solution obtained in the first polymerization step and the polymerizable monomers used in the second polymerization step.

When the polymerization initiator is added to the initial preparation mixture (1) to initiate the polymerization and then monomer mixture (2) and the polymerization initiator are gradually added and mixed thereto to initiate the polymerization, the addition and mixing are preferably carried out by dropwise, and the drop hour is preferably 20-300 minutes, more preferably 40-200 minutes, still more preferably 60-120 minutes. The temperature of the reaction system in the addition and mixing is preferably 30-200° C., more preferably 50-150° C.

The polymerization of the polymer solution (i.e., the above (1a) and (2a)) obtained in the first polymerization step is preferably stopped when the solution is used in the second polymerization step, and the total polymerization rate of the polymerizable monomers at that time is preferably 50-90%, more preferably 55-85%, still more preferably 60-80%. Examples of the method for stopping the polymerization include a method comprising adding a polymerization inhibitor to the polymer solution obtained in the first polymerization step, and a method comprising lowering the temperature of the polymer solution.

Examples of the polymerization inhibitor which may be used for stopping the polymerization include phenols such as hydroquinone, hydroquinone monomethyl ether, 2,5-bis(1,1,3,3-tetramethylbutyl)hydroquinone, 2,5-bis(1,1-dimethylbutyl)hydroquinone, methoxyphenol, 6-tert-butyl-2,4-xylenol, and 3,5-ditert-butylcatechol; N-nitrosophenylhydroxylamine aluminum salt; and phenothiazine, and any one of them may be used alone or in combination of two or more of them. Preferable examples of the polymerization inhibitor include phenols, and more preferable examples include hydroquinone monomethyl ether. The total amount to be used is preferably 1-10000 ppm, more preferably 10-1000 ppm, still more preferably 20-200 ppm relative to the polymerizable monomers used in the first polymerization step. When the total amount of the polymerization inhibitor to be used is less than 1 ppm, the polymerization may not be efficiently stopped. Meanwhile, when the total amount to be used is more than 10000 ppm, the polymerization of the second polymerization step may not be initiated.

The polymerization of the first polymerization step can be substantially stopped by lowering the temperature of the polymer solution to 40° C. or less. The degradation rate of the polymerization initiator depends on the temperature, and thus a radical is hardly produced when the temperature of the polymer solution is 40° C. or less. In order to more certainly stop the polymerization, the temperature of the polymer solution may be lowered to 20° C. or less.

Hereinafter, raw materials used in a preferable method for preparing the star-shaped acrylic block polymer are described in detail.

The (meth)acrylic acid alkyl ester having 7-17 carbon atoms accounts for 30-99.9% by mass (typically, 50-99.9% by mass) in the total amount to be used of the polymerizable monomers which may be used in the present invention. The total content of the (meth)acrylic acid alkyl ester having 7-17 carbon atoms in all polymerizable monomers is preferably 60-99.9% by mass, 35-97.0% by mass, more preferably 70-99.9% by mass, 40-95.0% by mass, more preferably 80-99.9% by mass, 42-90.0% by mass, especially preferably 90-99.9% by mass, 50-86% by mass. When the total content of the (meth)acrylic acid alkyl ester having 7-17 carbon atoms in all polymerizable monomers is less than 50% by mass (typically, less than 30% by mass), the obtained polymer does not have sufficiently adhesive force.

The preferable specific examples of the (meth)acrylic acid alkyl ester having 7-17 carbon atoms are as stated above, and any one of them may be used alone or in combination of two or more of them. The (meth)acrylic acid alkyl ester having 7-17 carbon atoms may be used in any step of the multistep radical polymerization steps, and preferably used in the second polymerization step (or the final polymerization step in case there are three or more polymerization steps).

The polymerizable monomer which may be used in the present invention may comprise a polymerizable monomer other than the (meth)acrylic acid alkyl ester having 7-17 carbon atoms (i.e., the weakly basic monomers and the other polymerizable monomers) at the content of less than 70% by mass (typically, less than 50% by mass) in the total amount to be used.

Preferable specific examples of the weakly basic monomer are as stated above, and any one of them may be used alone or in combination of two or more of them. The weakly basic monomer may be used in any step of the multistep radical polymerization steps, and preferably used in the second polymerization step (or the final polymerization step in case there are three or more polymerization steps).

The content of the weakly basic monomer which may be used in the present invention in all polymerizable monomers is 0.1-39% by mass, preferably 1-39% by mass (typically 1-35% by mass), more preferably 1.5-39% by mass (typically 1.5-32% by mass).

Also, the total content of the weakly basic monomer is 0.1-39% by mass, preferably 1-39% by mass (typically, 1-35% by mass), more preferably 1.5-39% by mass (typically, 1.5-32% by mass) relative to whole structural units of said star-shaped acrylic block polymer. When the total content of the weakly basic monomer is less than 0.1% by mass, a salt of a basic drug is not converted into a free base. Meanwhile, when the total content of the weakly basic monomer is more than 39% by mass, the balanced physical properties of the adhesive polymer are impaired.

Examples of the other polymerizable monomers include polymerizable monomers which are homopolymerizable or copolymerizable by radical polymerization, and preferable specific examples are as stated above, and any one of them may be used alone or in combination of two or more of them. The other polymerizable monomers may be used in any step of the multistep radical polymerization step, and preferably used in the first and the second polymerization steps (or all polymerization steps in case there are three or more polymerization steps).

In a preferable method for preparing the star-shaped acrylic block polymer, radical polymerization in the presence of a polyvalent mercaptan is carried out in multistep comprising two or more steps, and different kinds of polymerizable monomers are preferably used in each elementary step. In this case, the "different kinds of polymerizable monomers" mean not only polymerizable monomers having different chemical structures, but also combinations of polymerizable monomers having the same chemical structure in different mixture ratio. Examples of using different kinds of polymerizable monomers in each elementary step include using a combination of polymerizable monomers consisting of methyl methacrylate (90 parts by mass) and butyl acrylate (10 parts by mass) in the first polymerization step, and a combination of polymerizable monomers consisting of methyl methacrylate (10 parts by mass) and butyl acrylate (90 parts by mass) in the second polymerization step. In this case, the obtained star-shaped acrylic block polymer has chain polymer portions having very different glass transition temperatures (Tg), and can sufficiently achieve the effects of the present invention, and has practically high performance.

Examples of the polyvalent mercaptan which may be used in the above method include diesters of diols such as ethylene glycol and 1,4-butanediol and carboxyl group-containing mercaptans such as ethylene glycol dithioglycolate, ethylene glycol dithiopropionate, 1,4-butanediol dithioglycolate, and 1,4-butanediol dithiopropionate; triesters of triols such as trimethylolpropane and carboxyl group-containing mercaptans such as trimethylolpropane trithioglycolate and trimethylolpropane trithiopropionate; polyesters of compounds having four hydroxy groups such as pentaerythritol and carboxyl group-containing mercaptans such as pentaerythritol tetrakisthioglycolate and pentaerythritol tetrakisthiopropionate; polyester compounds of compounds having six hydroxy groups such as dipentaerythritol and carboxyl group-containing mercaptans such as dipentaerythritol hexakisthioglycolate and dipentaerythritol hexakisthiopropionate (alias: dipentaerythritol-β-mercaptopropionate) (hereinafter abbreviate as DPMP); other polyester compounds of compounds having three or more hydroxy groups and carboxyl group-containing mercaptans; compounds having three or more mercapto groups such as trithioglycerin; triazine polyvalent thiols such as 2-di-n-butylamino-4,6-dimercapto-S-triazine and 2,4,6-trimercapto-S-triazine; compounds wherein hydrogen sulfide is added to two or more epoxy groups of polyvalent epoxy compounds to introduce two or more mercapto groups; ester compounds prepared by esterification of two or more carboxyl groups of polyvalent carboxylic acids and mercaptoethanol; and the like, and any one of them may be used alone or in combination of two or more of them. Preferable polyvalent mercaptan is a mercaptan having three or more valences, and preferable examples of the polyvalent mercaptan include polyester compounds of compounds having six hydroxy groups such as dipentaerythritol or compounds having four hydroxy groups such as pentaerythritol and carboxyl group-containing mercaptans, and more preferable examples include dipentaerythritol hexakisthioglycolate, dipentaerythritol hexakisthiopropionate (alias: dipentaerythritol-β-mercaptopropionate) (hereinafter abbreviate as DPMP), pentaerythritol tetrakisthioglycolate, and pentaerythritol tetrakisthiopropionate, and more preferable examples include dipentaerythritol hexakisthiopropionate. In said examples, "carboxyl group-containing mercaptans" mean compounds having one mercapto group and one carboxyl group such as thioglycolic acid, mercaptopropionic acid, and thiosalicylic acid.

In all polymerization steps, the temperature in carrying out the radical polymerization is preferably 30-200° C., more preferably 50-150° C.

A conventional polymerization initiator may be used in the radical polymerization. Examples of the polymerization initiator include azo initiators such as dimethyl-2,2'-azobis(2-methylpropionate) (abbreviate as V-601), 2,2'-azobisisobutyronitrile, 2,2'-azobis(2-methylbutyronitrile), 2,2'-azobis(2,4-dimethylvaleronitrile), and dimethyl 2,2'-azobisisobutyrate; peroxide polymerization initiators such as benzoyl peroxide; and the like, and any one of them may be used alone or in combination of two or more of them. Preferable examples of the polymerization initiator include dimethyl-2,2'-azobis(2-methylpropionate) (V-601). The total amount of the polymerization initiator used in the radical polymerization is preferably ⅓ or less, more preferably ⅕ or less of the amount of the polyvalent mercaptan by mass ratio. When the polymerization initiator is used at the amount more than the above ratio, many polymers are also produced from the polymerization initiator in addition to chain polymer portions produced from a sulfur residue of a mercapto group, and the production efficiency of the star-shaped acrylic block polymer easily decreases, and the physical properties of the obtained star-shaped acrylic block polymer are also easily impaired. The polymerization initiator may be added to the reaction system at one time or in several divided parts. In case of adding in several divided parts, each part may be added at one time or added sequentially.

A conventional solvent may be used in the radical polymerization. Examples of the solvent include ester solvents such as ethyl acetate, propyl acetate, and butyl acetate; ketone solvents such as methyl ethyl ketone and cyclohexanone; aromatic solvents such as benzene and toluene; cellosolve solvents such as methyl cellosolve and ethyl cellosolve; and the like, and any one of them may be used alone or in combination of two or more of them.

In an especially preferable method for preparing the star-shaped acrylic block polymer, a booster is preferably subsequently added after the provision of all polymerizable monomers used in the second polymerization step (or the final polymerization step in case there are three or more polymerization steps) to a reaction system is completed. Examples of the booster include the above polymerization initiators, and any one of them may be used alone or in combination of two or more of them. The total amount of the booster to be used is not especially limited, and preferably 0.1-5% by mass, more preferably 0.2-2% by mass, still more preferably 0.3-1% by mass relative to the total amount of the polymerizable monomers to be used. When the total amount of the booster to be used is less than 0.1% by mass, the booster cannot exert the effect. Meanwhile, using the total amount of more than 5% by mass of booster is uneconomical, because many substances having low molecular weight are produced, and the physical properties of the polymer are deteriorated. Examples of the method for adding the booster is not especially limited, and include the continuously dropping method in which the booster is continuously added dropwise, and the dividedly dropping method in which the booster is added at specific time interval. The temperature in adding the booster is not especially limited, and preferably 30-200° C., more preferably 50-150° C. The addition time of the booster is not especially limited, and preferably 1-10 hours, more preferably 2-8 hours.

After the addition of the booster is completed, the reaction system may be further maturated preferably at 30-200° C., more preferably at 50-150° C. Specifically, the maturation is preferably carried out under a reflux condition (i.e., within the above temperature range) of a solvent to be used. The maturation time is not especially limited, and preferably 1 hour or more, more preferably 2 hours or more, still more preferably 3 hours or more. The upper limit of the maturation hours is not especially limited, and usually preferably within 20 hours.

In an especially preferable method for preparing the star-shaped acrylic block polymer, the total time from the start of the polymerization to the completion of the above maturation in the second polymerization step is preferably 8-20 hours, more preferably 12-20 hours, still more preferably 15-20 hours. The total time of less than 8 hours from the start of the polymerization to the completion of the above maturation in the second polymerization step is not preferable, because the effects of the present invention cannot be sufficiently achieved in the obtained star-shaped acrylic block polymer, and especially, the remained amount of the (meth)acrylic acid alkyl ester having 7-17 carbon atoms increases. The total time of more than 20 hours from the start of the polymerization to the completion of the above maturation in the second polymerization step is also not preferable, because the productivity significantly decreases, the energy cost increases, and the performance of the obtained star-shaped acrylic block polymer may also decrease.

In addition to the above method, a general method used in a conventional method for producing a star-shaped acrylic block polymer may be appropriately used as a preferable method for preparing the star-shaped acrylic block polymer.

The star-shaped acrylic block polymer is generally obtained as a polymer solution. When the star-shaped acrylic block polymer is obtained as a solution, the total non-volatile content in the solution is preferably 40-70% by mass, more preferably 45-65% by mass, still more preferably 45-60% by mass. When the total non-volatile content in the solution is less than 40% by mass, the viscosity of the solution decreases to cause the difficulty in coating the polymer, and such content is uneconomical because the amount of the solvent to be volatilized increases and much energy is required for drying. When the content is more than 70% by mass, the viscosity of the solution significantly increases to cause the difficulty in handling.

In the present invention, any one of the above adhesives may be used alone or in a mixture or two or more of them. Among them, an acrylic polymer and a star-shaped acrylic block polymer are preferable, and the star-shaped acrylic block polymer is especially preferable because of the excellently balanced adhesive force and cohesive force. The adhesive is added to an adhesive composition in the total amount of 50-99.9% by mass, preferably 50-99% by mass, more preferably 50-95% by mass.

The adhesive composition of the medical patch of the present invention may further comprise transdermal absorption enhancer etc. to increase the transdermal absorbability of a drug. Examples of the transdermal absorption enhancer include, but is not limited to, fatty acid esters such as isopropyl myristate, diisopropyl adipate, myristyl myristate, octyldodecyl myristate, isopropyl palmitate, butyl stearate, hexyl laurate, and decyl oleate; higher fatty acids such as caprylic acid, capric acid, isostearic acid, oleic acid, and myristic acid; amines such as diisopropanolamine and triethanolamine; polyvalent alcohol fatty acid esters such as propylene glycol monolaurate, propylene glycol fatty acid esters, glycerin fatty acid esters, sorbitan fatty acid esters, and sucrose fatty acid esters; polyvalent alcohols such as polyethylene glycol, propylene glycol, butylene glycol, and glycol; surfactants such as sorbitan monoleate, lauromacrogol, and lauryl alcohol; crotamiton, N-methylpyrrolidone, and the like, and any one of them may be used alone or in combination of two or more of them.

Further, an additive used in a conventional patch may be appropriately selected and used in the adhesive composition of the medical patch of the present invention if necessary in order to adjust the adhesive force and stability of the adhesive base. For example, water-soluble polymers such as polyvinylpyrrolidone and polyvinyl alcohol; cellulose derivatives such as ethylcellulose, hydroxypropyl cellulose, and hydroxypropyl methylcellulose; silicon compounds such as anhydrous silicic acid and light anhydrous silicic acid; inorganic fillers such as zinc oxide, aluminum oxide, magnesium oxide, iron oxide, titanium dioxide, and silica compounds; and antioxidants such as dibutylhydroxytoluene; and the like may be appropriately contained at an appropriate amount. Also, the adhesive composition of the medical patch of the present invention may comprise cross-linking agents, tackifiers, softeners, plasticizers, and the like if necessary. Further, the adhesive composition of the medical patch of the present invention may comprise preservatives, fresheners, fungicides, flavoring agents, coloring agents, and the like if necessary. These ingredients which may be used if necessary are not especially limited, and known ingredients are appropriately used at an appropriate amount.

Examples of the salt of the basic drug used in the medical patch of the present invention include carboxylates such as citrate, succinate, fumarate, maleate, and tartrate; and hydrochloride, sulfate, and phosphate of the basic drug, and include narcotic analgesics (for example, fentanyl citrate, morphine sulfate, oxycodone hydrochloride, or buprenorphine hydrochloride), urological agents (for example, oxybutynin hydrochloride, tamsulosin hydrochloride, or tolterodine tartrate), antiparkinsonian agents (rasagiline mesylate, pergolide mesylate, amantadine hydrochloride, trihexyphenidyl hydrochloride, or ropinirole hydrochloride), local anesthetics (for example, lidocaine hydrochloride or procaine hydrochloride), antidementia agents (for example, donepezil hydrochloride or memantine hydrochloride), psychoneurotic agents (for example, tandospirone citrate, methylphenidate hydrochloride, lurasidone hydrochloride, chlorpromazine hydrochloride, imipramine hydrochloride, or asenapine maleate), bronchodilators (for example, salbutamol sulfate, clenbuterol hydrochloride, tulobuterol hydrochloride, or procaterol hydrochloride), anti-inflammatory analgesics (for example, butorphanol tartrate or perisoxal citrate), antihypertensives (for example, enalapril maleate, propranolol hydrochloride, bisoprolol hydrochloride, or clonidine hydrochloride), coronary vasodilators (for example, diltiazem hydrochloride, verapamil hydrochloride, or isosorbide dinitrate), anti-allergic agents (for example, ketotifen fumarate, chlorpheniramine maleate, azelastine hydrochloride, or diphenhydramine hydrochloride), and serotonin receptor antagonists (for example, granisetron hydrochloride, ramosetron hydrochloride, palonosetron hydrochloride, and ondansetron hydrochloride). Any one of these drugs may be used alone or in combination of two or more of them, and may be added to the adhesive composition at the total amount of 0.1-50% by mass, preferably 1-50% by mass, more preferably 5-50% by mass.

The backing of the medical patch of the present invention is not especially limited, and an elastic or non-elastic backing usually used for a patch may be used. Specifically, a film or a sheet made from a synthetic resin such as polyethylene terephthalate, polyethylene, polypropylene, polybutadiene, ethylene vinyl acetate copolymer, polyvinyl chloride, polyester, nylon, and polyurethan, or a laminate thereof, a porous membrane, a foam, a woven fabric, a nonwoven fabric, a paper, or the like may be used.

In the medical patch of the present invention, the adhesive layer laminated on said backing is covered by a release liner, and the release liner is peeled off when the patch is used, and the surface of the adhesive layer is applied to a desired skin.

The release liner used in the patch of the present invention may be one usually used for a patch, and may be polyethylene terephthalate, polypropylene, a paper, or the like, and especially preferably polyethylene terephthalate. The release liner may be siliconized if necessary in order to optimize the peel force.

Also, the medical patch of the present invention may coexist with a deoxidant in order to enhance the stability of the drug during storage. Preferable examples of the deoxidant include a deoxidant made from iron and a deoxidant made from a non-ferrous metal. Examples of coexisting method of the deoxidant include a method wherein a deoxidant is directly included in a packaging container or a method wherein a deoxidizing film is laminated in a packaging container.

Examples of the method for preparing the medical patch of the present invention include the following method. A salt of a basic drug is dispersed in an appropriate solvent to prepare a drug solution. Separately, a star-shaped acrylic block polymer in which a weakly basic monomer is copolymerized, and other ingredients are mixed and dissolved or dispersed in an appropriate solvent to obtain an adhesive base. Examples of the solvent include toluene, ethyl acetate, ethanol, and methanol, and appropriately selected depending on ingredients, and any one of the solvents may be used alone or in a mixture of two or more. Subsequently, to the adhesive base is added the drug solution, and the mixture is homogeneously stirred and mixed to obtain an adhesive solution, and the adhesive solution is coated on a release liner or a backing, the solvent is removed by drying to obtain an adhesive layer, and then the adhesive layer is covered by a backing or a release liner to obtain a medical patch of the present invention. The thickness of the adhesive layer is 30-200 µm, more preferably 30-100 µm. When the thickness is less than 30 µm, the drug-release is not sustained for a long period of time. When the thickness is more than 200 µm, the drug content in the adhesive layer increases, which cause the increase in residual drug content and the increase in manufacturing cost.

Hereinafter, the present invention is described more in detail by way of Preparation examples and Examples, but the present invention is not limited to them. In the following Examples (Ex.) and Comparative examples (Comp.), "part(s)" and "%" mean "part(s) by mass" and "% by mass" respectively, unless otherwise specified. Also, the number average molecular weight (Mn) and the weight average molecular weight (Mw) were calculated by gel permeation chromatography (GPC) in a polystyrene equivalent.

EXAMPLES

Preparation of Acrylic Adhesive

Preparation Example 1

1. Polymerization in the First Step: Synthesis of the Intermediate Polymer Solution To a four neck flask having a thermometer, a stirrer, an inert gas inlet tube, a reflux cooler, and a dropping funnel were added methyl methacrylate (24 parts), dipentaerythritol-β-mercaptopropionate (hereinafter abbreviate as DPMP) (1.2 parts), and ethyl acetate (24.82 parts) as a solvent. The mixture was stirred under nitrogen stream and kept at 83±2° C., and to the mixture were added dimethyl-2,2'-azobis(2-methylpropionate) (trade name: V-601, manufactured by Wako Pure Chemical Industries, Ltd., hereinafter abbreviate as V-601) (0.048 parts) as a polymerization initiator and ethyl acetate (0.432 parts) as a solvent for dissolution to initiate the polymerization. After 30 minutes from the reaction initiation, to the mixture were added dropwise methyl methacrylate (56 parts) and ethyl acetate (15.25 parts) over 120 minutes, and added dropwise a V-601 solution (a mixture of V-601 (0.084 parts), DPMP (2.8 parts), and ethyl acetate (2.8 parts)) over 90 minutes, and a reaction was carried out with controlling the internal temperature under reflux. After the addition of methyl methacrylate was completed, to the mixture was added ethyl acetate (2 parts), and the reaction was carried out for additional 130 minutes. Subsequently, to the mixture was added a polymerization inhibitor solution (a mixture consisting of hydroquinone monomethyl ether (0.04 parts) and ethyl acetate (0.36 parts)) and ethyl acetate (38.431 parts) for dilution, and the mixture was cooled to obtain an intermediate polymer solution (A1) for an adhesive. The obtained intermediate polymer solution (A1) had a non-volatile content of 34.5%, and a viscosity of 90 mPa·s.

2. Reaction in the Second Step: Synthesis of Polymer for Adhesive

To a four neck flask having a thermometer, a stirrer, an inert gas inlet tube, a reflux cooler, and a dropping funnel were added the intermediate polymer solution (A1) (15.22 parts) obtained in the above reaction, butyl acrylate (8.49 parts), 2-ethylhexyl acrylate (6.85 parts), vinyl acetate (1.10 parts), dimethylaminoethyl methacrylate (10.96 parts), and ethyl acetate (11 parts) as a solvent. The mixture was stirred under nitrogen stream and kept at 83±2° C., and to the mixture was added a V-601 solution (a mixture of V-601 (0.02 parts) and ethyl acetate (1 part)) as a polymerization initiator to initiate the polymerization. After 10 minutes from the reaction initiation, to the mixture was added dropwise a monomer mixture consisting of the intermediate polymer solution (A1) (15.22 parts), butyl acrylate (8.49 parts), 2-ethylhexyl acrylate (6.85 parts), vinyl acetate (1.10 parts), dimethylaminoethyl methacrylate (10.96 parts), and ethyl acetate (10 parts) as a solvent, and a V-601 solution (a mixture of V-601 (0.02 parts) and ethyl acetate (4 parts)) over 80 minutes, and a reaction was carried out with control under reflux. After completion of the addition, to the mixture was added ethyl acetate (1 part), and the reaction was carried out for additional 3.5 hours. Subsequently, to the mixture was added dropwise a V-601 solution (a mixture of V-601 (0.08 parts) and ethyl acetate (4 parts)) as a booster over 1 hour, and the reaction was carried out under reflux for additional 10 hours. Subsequently, to the mixture was added ethyl acetate (20.3 parts) as a dilution solvent, and the mixture was cooled to obtain a polymer solution (B1) for an adhesive. The obtained polymer solution (B1) had a non-volatile content of 47.6%, and a viscosity of 500 mPa·s. The obtained polymer had a number average molecular weight (Mn) of 30,000, and a weight average molecular weight (Mw) of 77,000.

Also, the properties used in the above Preparation example were measured and evaluated by the following methods.
[Measurement Methods of Specs of Adhesives]
(1) Viscosity Viscosity was measured by a type B viscometer at 25° C. The number of revolutions was 12 revolutions per minute.
(2) Non-Volatile Content A mixture was dried at 150° C. for 15 minutes in a circulating hot air dryer, and a non-volatile content was calculated by mass change.

Preparation of Patch

Example 1

Rasagiline mesylate was dispersed in ethyl acetate to prepare a drug solution. Subsequently, to the acrylic adhesive obtained in Preparation example 1 was added the drug solution, and the mixture was homogeneously stirred and mixed to obtain an adhesive composition, and the adhesive composition was coated on a release liner and dried to remove the solvent and form an adhesive layer having a thickness of 30 μm, and then the adhesive layer was covered by a backing to prepare a medical patch. The amount of each ingredient is shown in Table 1-1.

Example 2

A medical patch of Example 2 was prepared according to the production method of Example 1 using the ingredients shown in the following Table 1-1 except that rasagiline mesylate was replaced with asenapine maleate.

Comparative Examples 1-7

Rasagiline mesylate was dispersed in ethyl acetate to prepare a drug solution. Subsequently, to an acrylic adhesive DURO-TAK 87-4098 (manufactured by Henkel) or DURO-TAK 87-9301 (manufactured by Henkel) was added the drug solution, and further added one kind of basic additive selected from diethanolamine, sodium acetate, and EUDRAGIT E-100 (aminoalkyl methacrylate polymer), and the mixture was homogeneously stirred and mixed to obtain an adhesive composition, and the adhesive composition was coated on a release liner and dried to remove the solvent and form an adhesive layer having a thickness of 30 μm, and then the adhesive layer was covered by a backing to prepare a medical patch. The amount of each ingredient is shown in Table 1-2 and Table 1-3.

Comparative Examples 8-10

Each medical patch of Comparative examples 8-10 was prepared according to the production method of the above Comparative examples 1-7 using the ingredients shown in the following Table 1-4 except that rasagiline mesylate was replaced with asenapine maleate.

The ingredients of the medical patch of Examples (Ex.) 1-2 and Comparative examples (Comp.) 1-10 are shown in the following [Table 1-1] to [Table 1-4].

TABLE 1-1

| Ingredient | Ex. 1 | Ex. 2 |
|---|---|---|
| Acrylic adhesive of Preparation example 1 | 90 | 85.2 |
| Rasagiline mesylate | 10 | — |
| Asenapine maleate | — | 14.8 |
| Total | 100 | 100 |
| Molar ratio of basic monomers relative to drug | 5 | 5 |

TABLE 1-2

| Ingredient | Comp. 1 | Comp. 2 | Comp. 3 |
|---|---|---|---|
| DURO-TAK 87-4098 | 70 | 74 | 36 |
| Diethanolamine | 20 | — | — |
| Sodium acetate | — | 16 | — |
| EUDRAGIT E-100 | — | — | 54 |
| Rasagiline mesylate | 10 | 10 | 10 |
| Total | 100 | 100 | 100 |
| Molar ratio of basic additives (or basic monomers in case of EUDRAGIT E-100) relative to drug | 5 | 5 | 5 |

TABLE 1-3

| Ingredient | Comp. 4 | Comp. 5 | Comp. 6 | Comp. 7 |
|---|---|---|---|---|
| DURO-TAK 87-9301 | 70 | 74 | 36 | — |
| DURO-TAK 87-4098 | — | — | — | 90 |
| Diethanolamine | 20 | — | — | — |
| Sodium acetate | — | 16 | — | — |
| EUDRAGIT E-100 | — | — | 54 | — |
| Rasagiline mesylate | 10 | 10 | 10 | 10 |
| Total | 100 | 100 | 100 | 100 |
| Molar ratio of basic additives (or basic monomers in case of EUDRAGIT E-100) relative to drug | 5 | 5 | 5 | — |

TABLE 1-4

| Ingredient | Comp. 8 | Comp. 9 | Comp. 10 |
|---|---|---|---|
| DURO-TAK 87-4098 | 65.8 | 70.1 | 33.9 |
| Diethanolamine | 19.4 | — | — |
| Sodium acetate | — | 15.1 | — |
| EUDRAGIT E-100 | — | — | 51.3 |
| Asenapine maleate | 14.8 | 14.8 | 14.8 |
| Total | 100 | 100 | 100 |
| Molar ratio of basic additives (or basic monomers in case of EUDRAGIT E-100) relative to drug | 5 | 5 | 5 |

[Test Example 1]: Probe Tack Test

In order to evaluate the adhesive force (tack force) of the medical patch of the present invention, a probe tack test was carried out using each patch of Examples 1-2 and Comparative examples 1-10. A spherical probe having a diameter of 5 mm made of stainless steel approached each adhesive surface at the rate of 10 mm per minute, and contacted the adhesive surface for 10 seconds, and then the probe was peeled off at the rate of 300 mm per minute, and the load in peeling off was measured. The results of Example 1 and Comparative examples 1-6 are shown in Table 2-1, and the results of Example 2 and Comparative examples 8-10 are shown in Table 2-2. The results are shown by the ratio (%) of tack force relative tack force (100) of an adhesive alone which does not comprises a drug and an additive to evaluate the effect of the addition of the drug and additives on the adhesive composition.

TABLE 2-1

| Test Formulation | Tack force (relative to adhesive alone, %) |
|---|---|
| Example 1 | 108 |
| Comparative example 1 | 53 |
| Comparative example 2 | 51 |
| Comparative example 3 | 18 |
| Comparative example 4 | 31 |
| Comparative example 5 | 47 |
| Comparative example 6 | 36 |

TABLE 2-2

| Test formulation | Tack force (relative to adhesive alone, %) |
|---|---|
| Example 2 | 97 |
| Comparative example 8 | 69 |
| Comparative example 9 | 57 |
| Comparative example 10 | 1 |

As shown in the test results in Table 2, the patches of the present invention had higher tack force as compared to each patch of Comparative examples. Namely, these results demonstrate that the formulations of the present invention have excellent adhesive force, because the patches of the present invention do not need an additive used for the conversion of a salt of a basic drug into a free base and do not suffer the decrease in tack force from such additive.

[Test Example 2]: Peel Test

In order to evaluate the adhesive force (peel force) of the medical patch of the present invention, a peel test was carried out using each patch of Example 1 and Comparative examples 1-6. Each patch having a size of 1 cm×5 cm was applied to a stainless steel test plate polished by sandpaper (No. 300), and the load in peeling off at the rate of 300 mm per minute was measured. The results are shown in Table 3. The results are shown by the ratio (%) of peel force relative to the peel force (100) of an adhesive alone which does not comprise a drug and an additive to evaluate the effect of the addition of the drug and additives on the adhesive composition.

TABLE 3

| Test formulation | Peel force (relative to adhesive alone, %) |
|---|---|
| Example 1 | 71 |
| Comparative example 1 | 47 |
| Comparative example 2 | 28 |
| Comparative example 3 | 10 |
| Comparative example 4 | 27 |
| Comparative example 5 | 52 |
| Comparative example 6 | 28 |

As shown in the above test results, the patch of the present invention had high peel force as compared to each patch of Comparative examples. Namely, these results demonstrate that the formulations of the present invention have excellent adhesive force, because the patches of the present invention do not need an additive used for the conversion of a salt of a basic drug into a free base and do not suffer the decrease in peel force from such additive.

[Test Example 3] Thermostability (Adhesive Property)

Each formulation of Example 1 and Comparative examples 1 and 4 was stored at 60° C. for 2 weeks, and subjected to the same tests as Test example 1 and Test example 2 to evaluate the tack force and the peel force. The results are shown in Table 4. The results are shown by the ratio (%) of tack force or peel force relative to the tack force or the peel force (100) of an adhesive alone which does not comprise a drug and an additive to evaluate the effect of the addition of the drug and additives on the adhesive composition.

TABLE 4

| Test formulation | Tack force (relative to adhesive alone, %) | Peel force (relative to adhesive alone, %) |
|---|---|---|
| Ex. 1 | 116 | 71 |
| Comp. 1 | 5 | 1 |
| Comp. 4 | 8 | 1 |

As shown in the test results in Table 4, the patch of the present invention had higher tack force and peel force as compared to each patch of Comparative examples. Namely, these results demonstrate that the formulations of the present invention have excellent adhesive force, because the patches of the present invention do not need an additive used for the conversion of a salt of a basic drug into a free base and do not suffer the decrease in tack force and peel force from such additive.

Also, in the results of this test, while each adhesive force of Comparative examples significantly decreased as compared to the adhesive force obtained in Test example 1 or Test example 2, the adhesive force of Example 1 was almost comparable to the adhesive force of adhesive alone like the test results obtained in Test example 1 and Test example 2. These results demonstrate that the excellent effects of the present invention are maintained even after stored under severe storage conditions at a high temperature.

[Test Example 4]: In Vitro Hairless Rat Transdermal Permeation Test

In order to study the transdermal absorbability of rasagiline from the patch of the present invention, each patch of Example 1, Comparative example 3, and Comparative example 7 was subjected to an in vitro transdermal permeation test using a hairless rat. In the test, the thickness of the adhesive layer of each formulation was adjusted to 100 μm. An excised abdominal skin of a hairless rat (HWY series, 7 weeks old) was put on a Franz diffusion cell, and each test formulation cut into a round shape (Φ 14 mm) was applied thereto. The receptor side was filled with phosphate buffered saline, and hot water of 37° C. was circulated in the water jacket. The receptor solution was sampled with lapse of time, and the amount of rasagiline permeated the skin was measured by liquid chromatography, and the transdermal absorption rates (Flux: $\mu g/cm^2/h$) after 8 hours and 16 hours from the start of the test was calculated using the amount. The results are shown in Table 5.

TABLE 5

| Ex./Comp. | Transdermal absorption rate after 8 hours (Flux: $\mu g/cm^2/h$) | Transdermal absorption rate after 16 hours (Flux: $\mu g/cm^2/h$) |
| --- | --- | --- |
| Ex. 1 | 20.57 | 16.56 |
| Comp. 3 | 17.47 | 14.46 |
| Comp. 7 | 0.82 | 0.81 |

As shown in the results in Table 5, the formulation of Comparative example 7, which does not comprise an additive used for converting rasagiline mesylate into a free base, had lower transdermal permeability of the drug, and transdermal permeability less than ½₀ as compared to Example 1. Namely, the patches of the present invention comprise star-shaped acrylic block polymers in which weakly basic monomers are copolymerized to sufficiently convert rasagiline mesylate into a free base, and thereby have excellent transdermal absorbability of the drug. Also, the formulation of Example 1 had comparable or higher transdermal absorbability as compared to the formulation of Comparative example 3, which comprises EUDRAGIT E-100 to convert the salt of the basic drug into the free base.

[Test Example 5]: Skin Primary Irritation Test in a Rabbit

A skin primary irritation test in a rabbit was carried out using the formulation of Example 1. The formulation was applied onto a dehaired rabbit back for 24 hours, and the Primary Irritation Index (P.I.I) was determined by the skin symptom at 1 hour, 24 hours, and 48 hours after peeling off. The results and the evaluation criteria are shown in Table 6 and Table 7 respectively.

TABLE 6

| Test formulation | Example 1 |
| --- | --- |
| Primary Irritation Index (P.I.I) | 1.8 |

TABLE 7

| P.I.I | Safety classification |
| --- | --- |
| P.I.I = 0 | Non irritant |
| 0 < P.I.I < 2 | Mild irritant |
| 2 ≤ P.I.I < 5 | Moderate irritant |
| 5 ≤ P.I.I | Severe irritant |

As shown in the results in Table 6, it was proved that the skin irritation of the patch of the present invention is very low. Namely, it was confirmed that the patches of the present invention do not comprise a basic additive for converting a salt of a basic drug into a free base, and do not suffer from the skin irritation caused by a basic additive per se and the skin irritation caused by a basic salt produced by the reaction of a basic additive and a salt of a basic drug, and thus are very safe patches.

Preparation of Acrylic Adhesive

Preparation Example 2

Alternative Reaction in the Second Step: Synthesis of Polymer for Adhesive

To a four neck flask having a thermometer, a stirrer, an inert gas inlet tube, a reflux cooler, and a dropping funnel were added the intermediate polymer solution (A1) (13.70 parts) obtained in Preparation example 1, butyl acrylate (15.04 parts), 2-ethylhexyl acrylate (6.16 parts), vinyl acetate (0.99 parts), dimethylaminoethyl methacrylate (2.47 parts), and ethyl acetate (11.5 parts) as a solvent. The mixture was stirred under nitrogen stream and kept at 83±2° C., and to the mixture was added a V-601 solution (a mixture of V-601 (0.03 parts) and ethyl acetate (1 part)) as a polymerization initiator to initiate the polymerization. After 10 minutes from the reaction initiation, to the mixture were added dropwise a monomer mixture consisting of the intermediate polymer solution (A1) (16.74 parts), butyl acrylate (18.38 parts), 2-ethylhexyl acrylate (7.53 parts), vinyl acetate (1.21 parts), dimethylaminoethyl methacrylate (3.01 parts), and ethyl acetate (11 parts) as a solvent, and a V-601 solution (a mixture of V-601 (0.02 parts) and ethyl acetate (4 parts)) over 80 minutes, and a reaction was carried out with control under reflux. After completion of the addition, to the mixture was added ethyl acetate (1 part), and the reaction was carried out for additional 3.5 hours. Subsequently, to the mixture was added dropwise a V-601 solution (a mixture of V-601 (0.08 parts) and ethyl acetate (4 parts)) as a booster over 1 hour, and the reaction was carried out under reflux for additional 10 hours. Subsequently, to the mixture was added ethyl acetate (30.3 parts) as a dilution solvent, and the mixture was cooled to obtain a polymer solution (B2) for an adhesive. The obtained polymer solution (B2) had a non-volatile content of 48.0%, a viscosity of 682 mPa·s, a number average molecular weight of 37,000, and a weight average molecular weight of 117,000.

Preparation Example 3

Alternative Reaction in the Second Step: Synthesis of Polymer for Adhesive

To a four neck flask having a thermometer, a stirrer, an inert gas inlet tube, a reflux cooler, and a dropping funnel were added the intermediate polymer solution (A1) (12.17 parts) obtained in Preparation example 1, butyl acrylate (14.43 parts), 2-ethylhexyl acrylate (5.48 parts), vinyl acetate (0.88 parts), dimethylaminoethyl methacrylate (1.10 parts), tetraethylene glycol diacrylate (0.035 parts), and ethyl acetate (11.5 parts) as a solvent. The mixture was stirred under nitrogen stream and kept at 83±2° C., and to the mixture was added a V-601 solution (a mixture of V-601 (0.02 parts) and ethyl acetate (1 part)) as a polymerization initiator to initiate the polymerization. After 10 minutes from the reaction initiation, to the mixture were added dropwise a monomer mixture consisting of the intermediate polymer solution (A1) (18.26 parts), butyl acrylate (21.64 parts), 2-ethylhexyl acrylate (8.22 parts), vinyl acetate (1.32 parts), dimethylaminoethyl methacrylate (1.64 parts), tetraethylene glycol diacrylate (0.053 parts), and ethyl acetate (11 parts) as a solvent, and a V-601 solution (a mixture of V-601 (0.02 parts) and ethyl acetate (4 parts)) over 80 minutes, and a reaction was carried out with control under reflux. After completion of the addition, to the mixture was added ethyl acetate (1 part), and the reaction was carried out for additional 3.5 hours. Subsequently, to the mixture was added dropwise a V-601 solution (a mixture of V-601 (0.17 parts) and ethyl acetate (20 parts)) over 5 hours as a booster, and the reaction was carried out under reflux for additional 10 hours. Subsequently, to the mixture was added ethyl acetate (14.3 parts) as a dilution solvent, and the mixture was cooled to obtain a polymer solution (B3) for an adhesive. The obtained polymer solution (B3) had a non-volatile content of 53.6%, a viscosity of 9,450 mPa·s, a number average molecular weight of 41,000, and a weight average molecular weight of 213,000.

Preparation Example 4

Alternative Reaction in the Second Step: Synthesis of Polymer for Adhesive

To a four neck flask having a thermometer, a stirrer, an inert gas inlet tube, a reflux cooler, and a dropping funnel were added the intermediate polymer solution (A1) (12.17 parts), obtained in Preparation example 1, butyl acrylate (13.37 parts), 2-ethylhexyl acrylate (5.48 parts), vinyl acetate (0.88 parts), dimethylaminopropyl acrylamide (2.19 parts), and ethyl acetate (11.5 parts) as a solvent. The mixture was stirred under nitrogen stream and kept at 83±2° C., and to the mixture was added a V-601 solution (a mixture of V-601 (0.02 parts) and ethyl acetate (1 part)) as a polymerization initiator to initiate the polymerization. After 10 minutes from the reaction initiation, to the mixture were added dropwise a monomer mixture consisting of the intermediate polymer solution (A1) (18.26 parts), butyl acrylate (20.05 parts), 2-ethylhexyl acrylate (8.22 parts), vinyl acetate (1.32 parts), dimethylaminopropyl acrylamide (3.29 parts), and ethyl acetate (11 parts) as a solvent, and a V-601 solution (a mixture of V-601 (0.02 parts) and ethyl acetate (4 parts)) over 80 minutes, and a reaction was carried out with control under reflux. After completion of the addition, to the mixture was added ethyl acetate (1 part), and the reaction was carried out for additional 3.5 hours. Subsequently, to the mixture was added dropwise a V-601 solution (a mixture of V-601 (0.17 parts) and ethyl acetate (12 parts)) as a booster over 3 hours, and the reaction was carried out under reflux for additional 10 hours. Subsequently, to the mixture was added ethyl acetate (63 parts) as a dilution solvent, and the mixture was cooled to obtain a polymer solution (B4) for an adhesive. The obtained polymer solution (B4) had a non-volatile content of 38.3%, and a viscosity of 14,410 mPa·s. However, the molecular weight could not be measured due to the clogging in the filtration process of a solution sample of the polymer solution (B4) in THF.

Preparation Example 5

Alternative Synthesis of Polymer for Adhesive

To a four neck flask having a thermometer, a stirrer, an inert gas inlet tube, a reflux cooler, and a dropping funnel were added butyl acrylate (14.09 parts), 2-ethylhexyl acrylate (5.25 parts), vinyl acetate (0.84 parts), dimethylaminoethyl methacrylate (0.82 parts), tetraethylene glycol diacrylate (0.002 parts), and ethyl acetate (31 parts) as a solvent. The mixture was stirred under nitrogen stream and kept at 83±2° C., and to the mixture was added a V-601 solution (a mixture of V-601 (0.03 parts) and ethyl acetate (1 part)) as a polymerization initiator to initiate the polymerization. After 10 minutes from the reaction initiation, to the mixture were added dropwise a monomer mixture consisting of butyl acrylate (32.87 parts), 2-ethylhexyl acrylate (12.25 parts), vinyl acetate (1.96 parts), dimethylaminoethyl methacrylate (1.91 parts), tetraethylene glycol diacrylate (0.005 parts), and ethyl acetate (21 parts) as a solvent, and a V-601 solution (a mixture of V-601 (0.06 parts) and ethyl acetate (4 parts)) over 80 minutes, and a reaction was carried out with control under reflux. After completion of the addition, to the mixture was added ethyl acetate (1 part), and the reaction was carried out for additional 3.5 hours. Subsequently, to the mixture was added dropwise a V-601 solution (a mixture of V-601 (0.17 parts) and ethyl acetate (12 parts)) as a booster over 3 hours, and the reaction was carried out under reflux for additional 10 hours. Subsequently, to the mixture was added ethyl acetate (20.3 parts) as a dilution solvent, and the mixture was cooled to obtain a polymer solution (B5) for an adhesive. The obtained polymer solution (B5) had a non-volatile content of 44.8%, a viscosity of 1,030 mPa·s, a number average molecular weight of 62,000, and a weight average molecular weight of 271,000.

Preparation Example 6

Alternative Synthesis of Polymer for Adhesive

To a four neck flask having a thermometer, a stirrer, an inert gas inlet tube, a reflux cooler, and a dropping funnel were added butyl acrylate (13.27 parts), 2-ethylhexyl acrylate (5.25 parts), vinyl acetate (0.84 parts), dimethylaminoethyl methacrylate (1.64 parts), tetraethylene glycol diacrylate (0.002 parts), and ethyl acetate (31 parts) as a solvent. The mixture was stirred under nitrogen stream and kept at 83±2° C., and to the mixture was added a V-601 solution (a mixture of V-601 (0.03 parts) and ethyl acetate (1 part)) as a polymerization initiator to initiate the polymerization. After 10 minutes from the reaction initiation, to the mixture were added dropwise a monomer mixture consisting of butyl acrylate (30.96 parts), 2-ethylhexyl acrylate (12.25 parts), vinyl acetate (1.96 parts), dimethylaminoethyl methacrylate (3.82 parts), tetraethylene glycol diacrylate (0.005 parts), and ethyl acetate (21 parts) as a solvent, and a V-601 solution (a mixture of V-601 (0.06 parts) and ethyl acetate (4 parts)) over 80 minutes, and a reaction was carried out with control under reflux. After completion of the addition, to the mixture was added ethyl acetate (1 part), and the reaction was carried out for additional 3.5 hours. Subsequently, to the mixture was added dropwise a V-601 solution (a mixture of V-601 (0.17 parts) and ethyl acetate (12 parts)) as a booster over 3 hours, and the reaction was carried out under reflux for additional 10 hours. Subsequently, to the mixture was added ethyl acetate (20.3 parts) as a dilution solvent, and the mixture was cooled to obtain a polymer solution (B6) for an adhesive. The obtained polymer solution (B6) had a non-volatile content of 45.2%, a viscosity of 509 mPa·s, a number average molecular weight of 53,000, and a weight average molecular weight of 202,000.

Preparation Example 7

Synthesis of Polymer for Adhesive

To a four neck flask having a thermometer, a stirrer, an inert gas inlet tube, a reflux cooler, and a dropping funnel were added butyl acrylate (13.27 parts), 2-ethylhexyl acrylate (5.25 parts), vinyl acetate (0.84 parts), dimethylaminopropyl acrylamide (1.64 parts), and ethyl acetate (41 parts) as a solvent. The mixture was stirred under nitrogen stream and kept at 83±2° C., and to the mixture was added a V-601 solution (a mixture of V-601 (0.03 parts) and ethyl acetate (1 part)) as a polymerization initiator to initiate the polymerization. After 10 minutes from the reaction initiation, to the mixture were added dropwise a monomer mixture consisting of butyl acrylate (30.97 parts), 2-ethylhexyl acrylate (12.25 parts), vinyl acetate (1.96 parts), dimethylaminopropyl acrylamide (3.82 parts), and ethyl acetate (31 parts) as a solvent, and a V-601 solution (a mixture of V-601 (0.06 parts) and ethyl acetate (4 parts)) over 80 minutes, and a reaction was carried out with control under reflux. After completion of the addition, to the mixture was added ethyl acetate (1 part), and the reaction was carried out for additional 3.5 hours. Subsequently, to the mixture was added dropwise a V-601 solution (a mixture of V-601 (0.17 parts) and ethyl acetate (12 parts)) as a booster over 3 hours, and the reaction was carried out under reflux for additional 10 hours. Subsequently, to the mixture was added ethyl acetate (20.3 parts) as a dilution solvent, and the mixture was cooled to obtain a polymer solution (B7) for an adhesive. The obtained polymer solution (B7) had a non-volatile content of 39.1%, and a viscosity of 4,090 mPa·s. However, the molecular weight could not be measured due to clogging in the filtration process of a solution sample of the polymer solution (B7) in THF.

Also, properties used in the above Preparation examples 2-7 were measured and evaluated by the method described in the above Preparation example 1.

Preparation of Patch

Example 3

The medical patch of Example 3 was prepared according to the production method in the above Example 1 using the ingredients shown in the following Table 8 except that the acrylic adhesive was replaced with the adhesive of Preparation example 2.

Example 4

The medical patch of Example 4 was prepared according to the production method in the above Example 1 using the ingredients shown in the following Table 8 except that the acrylic adhesive was replaced with the adhesive of Preparation example 3.

Example 5

The medical patch of Example 5 was prepared according to the production method in the above Example 1 using the ingredients shown in the following Table 8 except that the acrylic adhesive was replaced with the adhesive of Preparation example 4.

Comparative Example 11

The medical patch of Comparative example 11 was prepared according to the production method in the above Example 1 using the ingredients shown in the following Table 8 except that the acrylic adhesive was replaced with the adhesive of Preparation example 5.

Comparative Example 12

The medical patch of Comparative example 12 was prepared according to the production method in the above Example 1 using the ingredients shown in the following Table 8 except that the acrylic adhesive was replaced with the adhesive of Preparation example 6.

Comparative Example 13

The medical patch of Comparative example 13 was prepared according to the production method in the above Example 1 using the ingredients shown in the following Table 8 except that the acrylic adhesive was replaced with the adhesive of Preparation example 7.

The ingredients of the medical patches of Examples 3-5 and Comparative examples 11-13, and the molar ratio of basic monomers relative to drug, the tack force, the peel force, and the holding force of said medical patches are shown in the following Table 8.

TABLE 8

| Ingredient | Ex. 3 | Ex. 4 | Ex. 5 | Comp. 11 | Comp. 12 | Comp. 13 |
|---|---|---|---|---|---|---|
| Acrylic adhesive of Preparation example 2 | 97.5 | | | | | |
| Acrylic adhesive of Preparation example 3 | | 97.5 | | | | |
| Acrylic adhesive of Preparation example 4 | | | 97.5 | | | |
| Acrylic adhesive of Preparation example 5 | | | | 97.5 | | |
| Acrylic adhesive of Preparation example 6 | | | | | 97.5 | |
| Acrylic adhesive of Preparation example 7 | | | | | | 97.5 |
| Rasagiline mesylate | 2.5 | 2.5 | 2.5 | 2.5 | 2.5 | 2.5 |
| Total | 100 | 100 | 100 | 100 | 100 | 100 |
| Molar ratio of basic monomers relative to drug | 5.2 | 2.6 | 5.2 | 2.6 | 5.2 | 5.2 |

TABLE 8-continued

| Ingredient | Ex. 3 | Ex. 4 | Ex. 5 | Comp 11 | Comp. 12 | Comp. 13 |
|---|---|---|---|---|---|---|
| Tack force | ○ | ○ | ○ | Δ | Δ | ○ |
| Peel force | Δ | ○ | ○ | Δ | Δ | Δ |
| Holding force (seconds) | >7200 | >7200 | >7200 | 24 | 18 | 389 |

[Test Example 5]: Probe Tack Test

In order to evaluate the adhesive force (tack force) of the medical patch of the present invention, each patch of Examples 3-5 and Comparative examples 11-13 was subjected to a probe tack test according to the method in Test example 1. The results are shown in Table 8. In this test, some formulations of Comparative examples caused cohesive failure, and thus the physical properties were evaluated according to the 3 grade evaluation criteria shown in Table 9 using the comprehensive evaluation of the tack force and the presence of cohesive failure in the pasty preparation.

TABLE 9

| Evaluation division | Evaluation criteria |
|---|---|
| ○ | No cohesive failure was observed in pasty preparation, and the tack force was excellent. |
| Δ | A certain degree of cohesive failure was observed in pasty preparation. |
| x | Terrible cohesive failure was observed in pasty preparation, and a test could not be carried out. |

[Test Example 6]: Peel Test

In order to evaluate the adhesive force (peel force) of the medical patch of the present invention, each patch of Examples 3-5 and Comparative examples 11-13 was subjected to a peel test according to the method in Test example 2. The results are shown in Table 8.

[Test Example 7]: Holding Force Test

In order to evaluate the holding force of the medical patch of the present invention, each patch of Examples 3-5, and Comparative examples 11-13 was subjected to a holding force test. Each test formulation was cut into a size of 1 cm×5 cm, and the release film was peeled off, and the formulation was folded back at the point of 1 cm from the end of the longer direction to superpose two pasty preparation surfaces with each other. Subsequently, the residual 3 cm portion in which the pasty preparation surface was exposed was applied to a stainless steel 304-BA test plate, and a roller of 2 kg was reciprocated on the patch at the rate of 300 mm per minute, and the patch was left to stand for 20 minutes. Subsequently, a weight of 1 kg was mounted to the portion in which two pasty preparation surfaces were superposed with each other, and measured the elapsed time until the test formulation was completely peeled off from the test plate to evaluate the holding force. The elapsed time was measured up to 2 hours (7,200 seconds) from the start of the test. Each measurement value is shown in Table 8.

As shown in the above test results, the patches of the present invention had more excellent physical properties in the tack force, the peel force, and the holding force as compared to each patch of the Comparative examples. Especially, the patches of the present invention were far more excellent in the holding force as compared to the formulations of Comparative examples. It could be understood that these excellent cohesive and adhesive properties of the present patches are caused by the star-shaped acrylic block polymer of the present invention in which a weakly basic monomer is copolymerized.

[Test Example 8]: Drug-Release Test

In order to evaluate the drug-release property of the medical patch of the present invention, each patch of Example 3 and Comparative example 12 was subjected to a drug-release test. Each test formulation was punched into a round shape having a diameter of 14 mm (Φ 14 mm), and the backing side of each test formulation was applied to a slide glass using a double sided tape and fixed thereto. The test formulation fixed on the slide glass was put on a Franz diffusion cell in which the receptor bath was preliminarily filled with a test solution* so that the adhesive layer side contacted the receptor side, and the test solution was sampled with lapse of time, and the amount of rasagiline released to the test solution was measured by liquid chromatography, and the release rate (%)**, which is the rate of rasagiline released from the formulation, was calculated. The results are shown in Table 10.

*test solution: a mixed solution of 40% polyethylene glycol/10% isopropanol/ 50% phosphate buffered saline
**release rate: amount (mg) of rasagiline in test solution after 6 hours from the start of the test/content (mg) of rasagiline in test formulation (Φ 14 mm)×100

TABLE 10

| Test formulation | Drug-release rate (%) |
|---|---|
| Example 3 | 100.0 |
| Comparative example 12 | 85.4 |

As shown in the above test results, the patches of the present invention have excellent drug-release properties as compared to patches of Comparative examples, and have both of excellent formulation properties and drug-release properties.

INDUSTRIAL APPLICABILITY

According to the medical patch of the present invention comprising a star-shaped acrylic block polymer as an adhesive polymer, a medical patch, which has unimpaired formulation properties such as adhesive property and retention property of patch, low skin irritation, and a high drug-release property, can be provided.

The invention claimed is:
1. A medical patch comprising an adhesive composition comprising at least one salt of a basic drug and an adhesive, wherein the adhesive is a star-shaped acrylic block polymer having a star-shaped structure in which at least three chain polymer portions radiate from a polyvalent mercaptan residue situated at the center, wherein (meth)acrylic acid alkyl ester structural units having 7-17 carbon atoms account for 30-99.9% by mass of whole structural units of the star-shaped acrylic block polymer, and at least one of the chain polymer portions has a structural unit having a copolymer structure of polymerizable monomers comprising at least one (meth)acrylic acid alkyl ester having 7-17 carbon atoms and at least one weakly basic monomer selected from the group consisting of dimethylaminoethyl (meth)
acrylate, diethylaminoethyl (meth)acrylate, dimethylaminoethyl (meth)acrylate quaternary ammonium salt, dimethylaminopropyl acrylamide, diethylaminopropyl acrylamide, (meth)acrylamide, N-methyl(meth)acrylamide and N-propyl(meth)acrylamide;

wherein the at least one salt of the basic drug is at least one selected from the group consisting of fentanyl citrate, morphine sulfate, oxycodone hydrochloride, buprenorphine hydrochloride, oxybutynin hydrochloride, tamsulosin hydrochloride, tolterodine tartrate, rasagiline mesylate, pergolide mesylate, amantadine hydrochloride, trihexyphenidyl hydrochloride, ropinirole hydrochloride, lidocaine hydrochloride, procaine hydrochloride, donepezil hydrochloride, memantine hydrochloride, tandospirone citrate, methylphenidate hydrochloride, lurasidone hydrochloride, chlorpromazine hydrochloride, imipramine hydrochloride, asenapine maleate, salbutamol sulfate, clenbuterol hydrochloride, tulobuterol hydrochloride, procaterol hydrochloride, butorphanol tartrate, perisoxal citrate, enalapril maleate, propranolol hydrochloride, bisoprolol hydrochloride, clonidine hydrochloride, diltiazem hydrochloride, verapamil hydrochloride, isosorbide dinitrate, ketotifen fumarate, chlorpheniramine maleate, azelastine hydrochloride, diphenhydramine hydrochloride, granisetron hydrochloride, ramosetron hydrochloride, palonosetron hydrochloride and ondansetron hydrochloride; and wherein the adhesive composition does not comprise an additive used for converting the at least one salt of the basic drug into a free base.

2. The medical patch according to claim 1, wherein the content of the at least one weakly basic monomer relative to a non-volatile content in the adhesive is 0.1-39% by mass.

3. The medical patch according to claim 1, wherein the content of the at least one salt of the basic drug is 0.1-50% by mass, and the content of the adhesive is 50-99.9% by mass in the adhesive composition.

4. The medical patch according to claim 1, wherein the at least one (meth)acrylic acid alkyl ester having 7-17 carbon atoms is at least one selected from the group consisting of (meth)acrylic acid butyl ester, (meth)acrylic acid t-butyl ester, (meth)acrylic acid pentyl ester, (meth)acrylic acid hexyl ester, (meth)acrylic acid heptyl ester, (meth)acrylic acid octyl ester, (meth)acrylic acid isooctyl ester, (meth)acrylic acid nonyl ester, (meth)acrylic acid isononyl ester, (meth)acrylic acid decyl ester, (meth)acrylic acid undecyl ester, (meth)acrylic acid dodecyl ester and (meth)acrylic acid 2-ethylhexyl ester.

5. The medical patch according to claim 1, wherein the at least one salt of the basic drug is at least one selected from the group consisting of rasagiline mesylate and asenapine maleate.

6. The medical patch according to claim 1, wherein the at least one weakly basic monomer is selected from the group consisting of dimethylaminoethyl methacrylate and dimethylaminopropyl acrylamide.

* * * * *